US011179719B2

(12) United States Patent
Zagnoni et al.

(10) Patent No.: US 11,179,719 B2
(45) Date of Patent: Nov. 23, 2021

(54) MICROFLUIDIC DEVICE

(71) Applicant: UNIVERSITY OF STRATHCLYDE, Glasgow (GB)

(72) Inventors: Michele Zagnoni, Glasgow (GB); Theresa Christ, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 229 days.

(21) Appl. No.: 16/604,507

(22) PCT Filed: Apr. 11, 2018

(86) PCT No.: PCT/GB2018/050958
§ 371 (c)(1),
(2) Date: Oct. 10, 2019

(87) PCT Pub. No.: WO2018/189532
PCT Pub. Date: Oct. 18, 2018

(65) Prior Publication Data

US 2020/0164368 A1 May 28, 2020

(30) Foreign Application Priority Data

Apr. 13, 2017 (GB) ..................................... 1705982

(51) Int. Cl.
*B01L 3/00* (2006.01)
*C12M 3/06* (2006.01)

(52) U.S. Cl.
CPC ..... *B01L 3/50273* (2013.01); *B01L 3/502761* (2013.01); *B01L 2200/027* (2013.01);
(Continued)

(58) Field of Classification Search
CPC ........... B01L 3/50273; B01L 3/502761; B01L 2200/027; B01L 2200/04; B01L 2200/0647; B01L 2300/0816; C12M 23/16
See application file for complete search history.

(56) References Cited

U.S. PATENT DOCUMENTS

2011/0244565 A1 10/2011 Beebe
2016/0097028 A1 4/2016 Tung

FOREIGN PATENT DOCUMENTS

WO 2010101708 9/2010
WO 2012051218 4/2012
(Continued)

OTHER PUBLICATIONS

International Search Report and Written Opinion for International Patent Application No. PCT/GB2018/050958 dated Jul. 19, 2018, pp. 1-16.
(Continued)

*Primary Examiner* — Jennifer Wecker
*Assistant Examiner* — Kathryn Elizabeth Limbaugh
(74) *Attorney, Agent, or Firm* — Wolter Van Dyke Davis, PLLC; Eugene Molinelli

(57) ABSTRACT

A microfluidic device (10) comprising: a main body; at least one source reservoir and at least one collection reservoir (18,20); at least one fluid channel (12) for channelling a fluid comprising a compound from the at least one source reservoir (18) to the at least one collection reservoir (20); a plurality of chambers (13) for holding cells, wherein the plurality of chambers (13) are formed underneath and open to the fluid channel (12), wherein a fluid flow is generated through the at least one fluid channel (12) by a difference in hydrostatic pressure between fluid in the at least one source reservoir (18) and fluid the at least one collection reservoir (20) such that the fluid flow provides a compound concen-
(Continued)

tration gradient across the plurality of chambers (13) and wherein the at least one collection reservoir (20) has an overflow opening (32) to substantially maintain a level of hydrostatic pressure in the at least one collection reservoir (20).

23 Claims, 10 Drawing Sheets

(52) U.S. Cl.
CPC ... *B01L 2200/04* (2013.01); *B01L 2200/0647* (2013.01); *B01L 2300/0816* (2013.01); *C12M 23/16* (2013.01)

(56) References Cited

FOREIGN PATENT DOCUMENTS

| | | |
|---|---|---|
| WO | 2013115725 | 8/2013 |
| WO | 2015138034 | 9/2015 |

OTHER PUBLICATIONS

Int. Prelim. Rpt. on Patentability, in PCT application No. GB2018/050958, issued on Oct. 15, 2019, pp. 1-12.

Christ et al., Microfluidics Drug Dose Responses of 3D Cancer Spheroids in Microfluidicsthe, Medical Research Scotland, 2015, Program #: 926.17, 1 page.

Christ et al., On-Chip Formation of 3D Spheroids for Patient-Derived Tissue Screening, Medical Research Scotland, 2016, 1 page.

(a)

(b)

MICROFLUIDIC DEVICE

CROSS REFERENCE TO RELATED APPLICATIONS

This application is a 371 national stage application of PCT Application No. PCT/GB2018/050958, filed Apr. 11, 2018, and claims the benefit of GB application 1705982.5, filed Apr. 13, 2017, the entire contents of which are incorporated herein.

INTRODUCTION

The present invention relates to a microfluidic device and method for culturing and screening cells.

BACKGROUND

Tumours contain a heterogeneous cell population and grow in 3 dimensions, resulting in the formation of gas, nutrient and drug concentration gradients within tissue. Presently, cancer research and drug testing in industry and academia is mostly conducted on 2D cell monolayers. 2D cell monolayers lack the complexity of real tumours. Furthermore, research is carried out using cell lines, which poorly reflect tumour heterogeneity and genetic diversity.

Known techniques, including spinner flasks and hanging drop plates, render screening of patient-derived 3D spheroids in a high-throughput manner not possible.

SUMMARY

According to a first aspect of the present invention, there is provided a microfluidic device comprising a main body; at least one source reservoir and at least one collection reservoir; at least one fluid channel for channelling a fluid comprising a compound from the at least one source reservoir to the at least one collection reservoir; a plurality of chambers for holding cells, wherein the plurality of chambers are formed underneath and open to the fluid channel, wherein a fluid flow is generated through the at least one fluid channel by a difference in hydrostatic pressure between fluid in the at least one source reservoir and fluid in the at least one collection reservoir such that the fluid flow provides a compound concentration gradient across the plurality of chambers and wherein the at least one collection reservoir has an overflow opening, for example to substantially maintain a hydrostatic pressure in the at least one collection reservoir.

Advantageously, by substantially maintaining a hydrostatic pressure in the at least one collection reservoir, the compound concentration gradient is kept substantially constant over an extended period of time. The hydrostatic pressure in the at least one collection reservoir may change at a rate below a predetermined threshold value.

The microfluidic device may have a removable overflow plug sized to close the overflow opening when inserted into the overflow opening. By providing a removable overflow plug the opening can be arranged in a closed and an open configuration for creating a compound concentration gradient and substantially maintaining a compound concentration gradient.

At least one reservoir of the at least one source reservoir and the at least one collection reservoir may have an inlet for introducing fluid to said reservoir. All of the at least one source reservoirs may have an inlet. All of the at least one collection reservoirs may have an inlet. The inlets may be provided at an upper surface of the device. At least one reservoir of the at least one collection reservoir and the at least one source reservoir may be open at its upper end.

The at least one fluid channel may comprise a collection channel coupled to the at least one collection reservoir wherein the plurality of chambers are provided in the collection channel, and a plurality of further channels in fluid communication with the at least one source reservoir and coupled to the collection channel for channelling fluid from the at least one source reservoir to the collection channel. Advantageously, the fluid channels coupled to the collection channel provide a concentration gradient across a width of the collection channel.

The plurality of further channels may comprise at least one micro-channel. The plurality of further channels may comprise an array of micro-channels. Each micro-channel provides a hydraulic resistance to decrease fluid flow velocity through the micro-channel. Each micro-channel may have a hydraulic diameter below 1 mm.

The at least one fluid channel may comprise at least one secondary channel coupled to the at least one source reservoir and arranged to be substantially parallel to the collection channel, and wherein the plurality of further channels couple the at least one secondary channel to the at least one collection channel.

The at least one secondary channel may comprise two secondary channels positioned on either side of the collection reservoir. A concentration gradient can be further controlled by providing two secondary channels.

The collection channel may be coupled to two collection reservoirs and/or each of the at least one secondary channels may be coupled to two source reservoirs. By providing two reservoirs an even distribution may be provided.

The collection channel may be coupled to a first collection reservoir at a first end and a second collection reservoir at a second end. The at least one source channel may be coupled to a first source reservoir at a first end and a second source reservoir at a second end.

The at least one source reservoir may be sized to have a greater fluid capacity than the at least one collection reservoir. Advantageously the level of fluid in the at least one source reservoir decreases at a slower rate than the level of fluid in the at least one collection reservoir. The at least one source reservoir may be sized to have an at least four times greater fluid capacity than the at least one collection reservoir. The at least one source reservoir may be sized to be at least four, six or twelve times greater fluid capacity than the at least one collection reservoir.

The chambers of the plurality of chambers may be square, round, rectangular and/or oblong in shape. A square and/or round shape allows a 3D cell spheroid to be formed and/or seeded. An oblong and/or rectangular shape allows forming and/or seeding of a cell network in the chamber. The chambers may be arranged in an array having one or more columns and one or more rows. An array allows more than one cell sample to be simultaneously exposed to the compound concentration gradient. The array allows for patient-derived tissue screening to be performed.

Each chamber of the plurality of chambers may be a micro-well. Each chamber of the plurality of chambers may have a volume in the range of 100 to 400 micrometres cubed. Each chamber of the plurality of chambers may have a volume that is one of 100, 150, 250, 400 micrometres cubed.

The cell network may be two-dimensional or three-dimensional.

The device may comprise, and/or be fabricated using, at least one of polydimethylsiloxane (PDMS), polystyrene or polycarbonate.

The interior surfaces of the device may be non-adherent. Non-adherent interior surfaces promote formation of spheroids.

The compound concentration gradient across the plurality of chambers may be substantially continuous or substantially non-continuous. A substantially continuous gradient may be provided across an array of more than one chamber to measure the response of cells to a continuous variation in compound concentrations. A substantially non-continuous gradient may be provided for a cell network in an oblong and/or rectangular chamber to measure spread of a stimulus from one portion of the cell network to another portion of the cell network.

The reservoirs may be sized to allow a continuous or non-continuous compound concentration gradient to be created across the plurality of chambers. The reservoirs may be sized to allow a linear or a sharp compound gradient to be created across the array of chambers.

According to a second aspect of the present invention, there is provided a kit of parts to be assembled to form the microfluidic device according to the first aspect of the present invention said kit of parts comprising a lower layer and an upper layer sized to permit connection. The kit of parts may further comprise a middle layer sized to permit connection to the upper layer and to the lower layer.

According to a third aspect of the present invention, there is provided an assay system having at least one microfluidic device according to the first aspect of the present invention, imaging means for imaging seeded cells in the at least one microfluidic device and a well plate. The imaging means may be fluorescent imaging means. A second microfluidic device may be provided. The assay system may be used with a robotic dispenser with incubator to automate the assay.

According to a fourth aspect of the present invention, there is provided a method comprising seeding cells in a plurality of chambers formed underneath and open to a fluid channel, wherein the fluid channel is configured to channel fluid from at least one collection reservoir to at least one source reservoir; providing an overflow opening in the at least one collection reservoir; providing the at least one collection reservoir with a first volume of a first fluid and providing the at least one source reservoir with a second volume of a second fluid, wherein the second fluid comprises a compound, such that a fluid flow is generated by a difference in hydrostatic pressure between the first volume of first fluid in the at least one collection reservoir and the second volume of second fluid in the at least one source reservoir thereby providing a compound concentration across the plurality of chambers, wherein fluid exits through the overflow opening in the at least one collection reservoir to substantially maintain a level of hydrostatic pressure in the at least one collection reservoir.

According to a fifth aspect of the present invention, there is provided a method comprising seeding a plurality of sample cells in an oblong chamber to provide a cell network in the oblong chamber; applying a stimulus to a first portion, for example an end portion, of the cell network, and performing a measurement of a response of a second portion of the cell network to the stimulus.

The cell network may be two dimensional or three dimensional.

The stimulus may be a chemical stimulus. The response may be a positive or negative response. The measurement of a response may be performed after a first period of time.

BRIEF DESCRIPTION OF THE DRAWINGS

Various aspects of the invention will now be described by way of example only, and with reference to the accompanying drawings, of which.

DETAILED DESCRIPTION OF THE DRAWINGS

Figure 1:
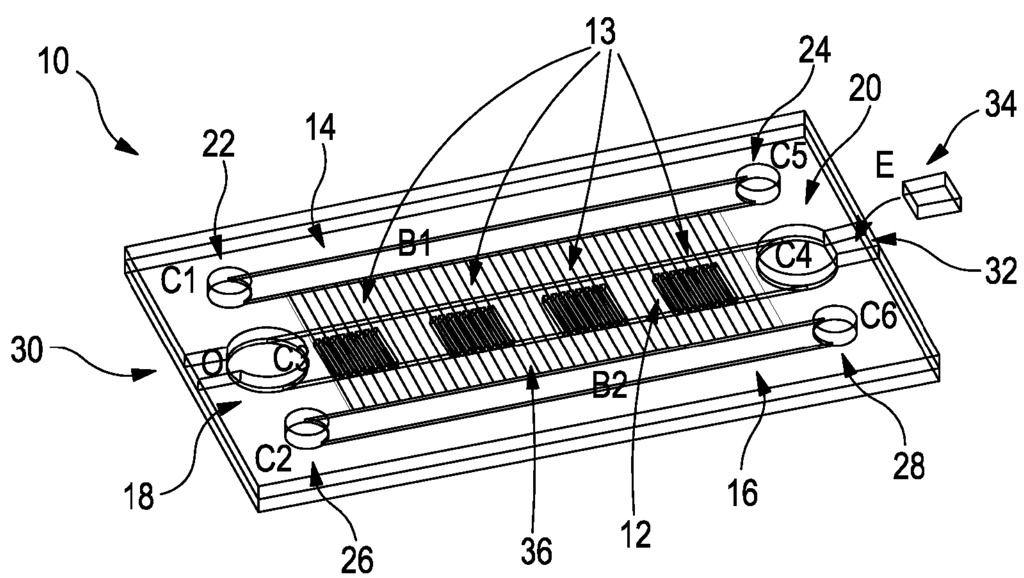
FIG. 1 is a perspective view of a microfluidic device in an assembled configuration.

FIG. 1 shows a microfluidic device 10. The microfluidic device 10 is a multi-layered structure. FIG. 1 shows the microfluidic device 10 in an assembled configuration. The device 10 is a substantially flat rectangular cartridge. The device 10 can be assembled from multiple parts configured to fit together, as described with reference to FIG. 7.

The device 10 has a central fluid channel 12 extending along its length. Four arrays of chambers, in this embodiment micro-wells 13, suitable, for example, for the culture of 3D multicellular spheroids, are provided in a bed of the central fluid channel 12. Each array of micro-wells 13 is formed such that the micro-wells are underneath the bed of the central channel 12 and open at an upper end to the central channel 12. Substantially along a first edge and a second edge of the device and on either side of the central channel 12 there is provided a first side channel 14 and a second side channel 16. The first side channel 14 and second side channel 16 have an equal length, equal depth and equal width and extend parallel to each other and parallel to the central channel 12.

Each channel 12, 14, 16 is level and contained within the device 10. Relative to the upper surface of the device 10, the side channels 14 and 16 are provided at a side channel depth. Likewise, the central channel 12 is provided at a central channel depth.

Each channel 12, 14, 16 has two associated cylindrical reservoirs 18, 20, 22, 24, 26, 28 provided at either end of the channel. The associated reservoirs are coupled to their associated channel such that the reservoirs can collect fluid from and/or provide fluid for their associated channels. The reservoirs can also store fluid. When fluid is in a channel and stored in the associated reservoirs, the reservoirs at both ends of the channel act to exert a hydrostatic pressure on fluid in the channel at both ends, thereby holding the fluid in the channel at a hydrostatic pressure. The cylindrical reservoirs are wells formed in the device that extend from the upper surface of the device 10 to the depth of their associated channels. The cylindrical reservoirs 18, 20, 22, 24, 26, 28 are open at the upper surface of the device 10, such that the openings of the reservoirs provide inlets to their associated channel. The volume and therefore capacity for holding and storing fluid of cylindrical reservoirs 18, 20, 22, 24, 26, 28 is determined by reservoir depth and surface area of inlet.

In further detail, the central channel 12 has a first central reservoir 18 at its first end and a second central reservoir 20 at its second end. Both central reservoirs 18, 20 have an equal volume and therefore equal capacity for holding fluid. The first central reservoir 18 is coupled to a first overflow opening 30. Likewise the second central reservoir 20 is coupled to a second overflow opening 32. The overflow openings 30, 32 can be closed by a first and second overflow plug or cap 34. For example, the overflow openings 30, 32 can be closed during cell culture and opened for compound concentration gradient formation. The dimensions of the overflow openings 30, 32 when open, determine the volume of the liquid that the reservoirs 18, 20 can hold and influences compound concentration gradient duration. FIG. 1 shows a second overflow plug 34 for the second overflow opening 32.

The first side channel 14 has a first side reservoir 22 and a second side reservoir 24 at its first and second end, respectively. The second side channel 16 has a first side reservoir 26 and a second side reservoir 28 at its first and second end, respectively. Each side reservoir 22, 24, 26, 28 has an equal capacity for holding fluid.

The side reservoirs 22, 24, 26, 28 have a higher capacity for holding fluid than the central reservoirs 18, 20. As a non-limiting example, the side reservoirs may have a value of 4, 8 or 12 times the capacity of the central reservoirs.

A network of micro-channels, here depicted as a rectangular array of micro-channels 36, are coupled to the first and second side channels 14, 16 and to central channel 12. The rectangular array of micro-channels 36 is an array of parallel micro-channels of equal length. Each micro-channel has a first and second end. The array of micro-channels 36 is oriented such that the micro-channels are provided perpendicular to the parallel lengths of the side channels 14, 16 and central channel 12. Each micro-channel is sized so that its first end is coupled to the first side channel 14 and its second end coupled to the second side channel 16. Each micro-channel may have a hydraulic diameter below 1 mm.

As the central channel 12 is provided at a lower depth in the device 10 to the side channels, the micro-channels 36 coupled to the side-channels bridge over the central channel 12. The micro-channels 36 have an opening to the central channel on their lower surfaces. Likewise, the central channel 12 has a corresponding opening to the micro-channels on its upper surface. These openings overlap such that fluid can flow from the first side channel 14 to the central channel 12 and fluid from the second side channel 16 can flow to the central channel 12 via the micro-channels 36. Fluid flow directions are controlled by controlling hydrostatic pressure.

The device unit of FIG. 1 can be replicated many times to fit within the format of a well plate. The number of device units fitted in a well-plate is limited by the size of the device units. The size of the device unit is dependent on, for example, the size of the reservoirs of the device unit.

Figure 2:
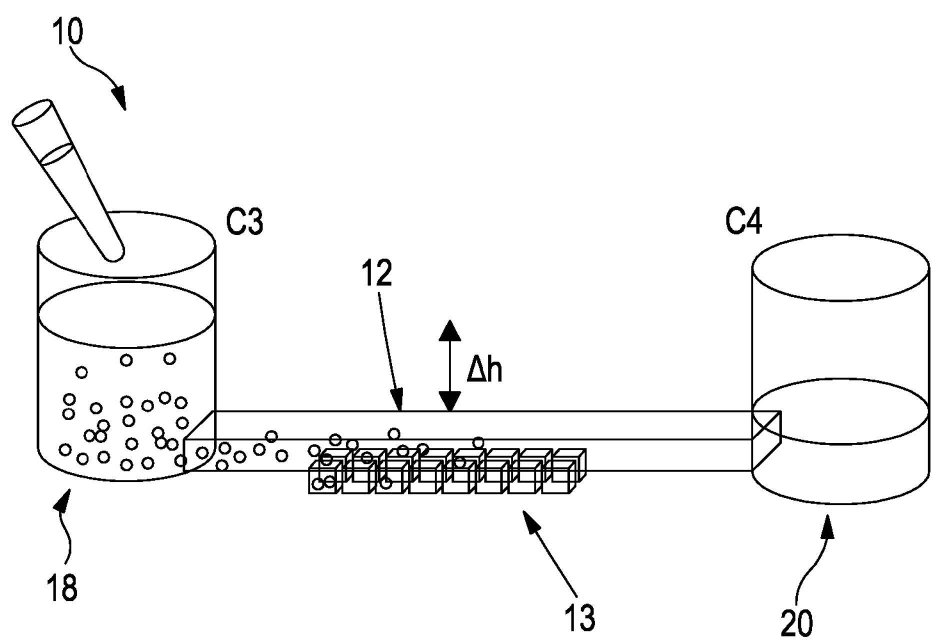
FIG. 2 is a schematic diagram of the microfluidic device illustrating a cell seeding procedure.

The device 10 can be used for cell seeding, in particular, for the formation of spheroids. FIG. 2 shows the device 10 being used for cell-seeding. FIG. 2 illustrates the central channel 12 in fluid communication with its associated first central reservoir 18 and second central reservoir 20. FIG. 2 also shows the array of micro-wells 13 provided in the central channel 12. Prior to cell seeding, interior surfaces of the central channel and the central reservoirs are coated with molecules and/or surfactant that render their surfaces non-adherent, thus preventing seeded cells from adhering to the interior surfaces of the device, thus promoting formation of spheroids.

To perform cell seeding, a fluidic medium is introduced into the first central reservoir 18 and into the second central reservoir 20 thereby to introduce the medium into the central channel 13. At this stage the amounts of medium introduced into the first and second reservoirs are equal such that, once the central channel 13 is full of medium, the first and second reservoirs have an equal volume of medium. In other words, both reservoirs are filled to an equal height. Due to the equal height of fluid, the first and second reservoirs contain columns of fluid that exert an equal hydrostatic pressure on fluid in the central channel 12.

Following the introduction of medium, cells in a cell suspension are then introduced into one of the two central reservoirs, for example the first central reservoir 18, as shown in FIG. 2. Injecting cell suspension in to the first central reservoir 18 produces a height difference between the fluid in the first reservoir 18 and fluid in the second reservoir 20. The first reservoir 18 contains a column of fluid that exerts a first hydrostatic pressure on the fluid at the first end of the central channel 12 and the second reservoir 20 contains a column of fluid that exerts a second hydrostatic pressure on the fluid at the second end of the central channel 12. Due to the height difference of the fluid in the first reservoir and the fluid in the second reservoir, labelled by $\Delta h$, the first hydrostatic pressure in first reservoir 18 is greater than the second hydrostatic pressure in second reservoir 20. A hydrostatic pressure difference or hydrostatic pressure gradient between the first and second reservoirs generates a fluid flow in the direction from the first reservoir to the second reservoir via the central channel 12.

As a non-limiting example, the volume of cell suspension solution injected into the first reservoir to create the height difference is in the range 5 micro-litres to 10 micro-litres, preferably 5 micro-litres or 10 micro-litres.

The fluid flow transports cells in the cell suspension along the central channel 12 and over the micro-well array 13. As the cells flow over the micro-wells, cells sediment into the micro-wells. The concentration of cells deposited inside the micro-wells depends on characteristics of the fluid, for example, concentration of the introduced cell suspension and characteristics of the flow generated by the device, for example, the flow velocity of the fluid.

Introduction of a cell suspension can be repeated, from either reservoir in order to enable formation of a desired seeding cell density inside the micro-wells. For example, repeated injections from either side influence the final seeding cell density inside the micro-wells and therefore to create spheroid of different sizes and shapes.

In addition to repeating injections, different micro-well dimensions and geometries and positioning can be used to create spheroids of different sizes and shapes and can be adapted for the type of assay to be performed.

Figure 3:
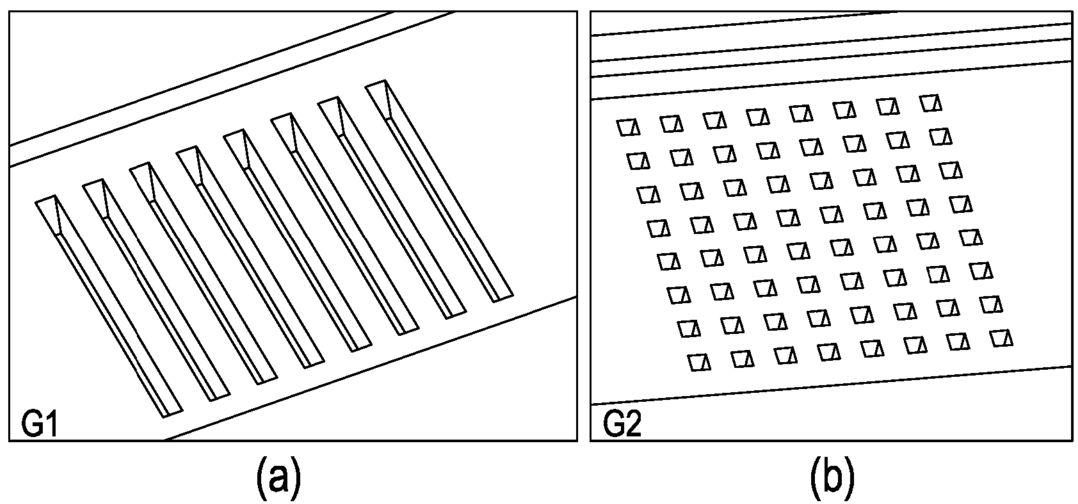
FIG. 3 shows two examples of micro-well arrays.

As an example, square or round micro-wells form round spheroids whereas rectangular micro-wells form oblong multi-cellular structures and directional cell networks. Differently sized spheroids enable analysis of drug effects according to spheroid size, informing on drug penetration. FIG. 3 shows two examples of different well shapes. FIG. 3(*a*) shows an array of rectangular shape. The array has eight rectangular micro-wells arranged in a parallel configuration. FIG. 3(*b*) shows an array of wells of squared shape. The array is an 8×8 square array of square micro-wells. The arrangement, position and size of the micro-wells are dependent on the type of assay to be performed.

Figure 4:
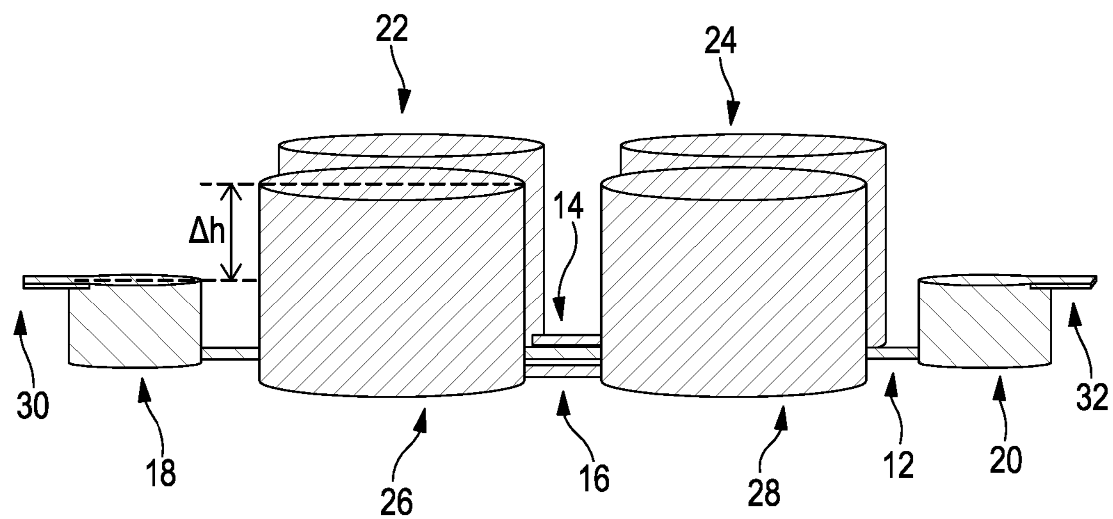
FIG. 4 is a further schematic diagram of the microfluidic device.

Device 10 is used to generate a compound concentration gradient over the array of micro-wells, and hence over the seeded cells contained in the micro-wells. FIG. 4 shows a schematic diagram of the first side channel 14 and associated reservoirs 22, 24 and the second side channel 16 and associated reservoirs 26, 28. Also shown in FIG. 4, is the first central reservoir 18 and the second central reservoir 20 connected together by the central channel 12. The first overflow opening 30 of the first reservoir 18 and the second overflow opening 32 of the second reservoir 20 are also shown. Not shown in FIG. 4 is the network of micro-channels 36 that couple the side channels 14 and 16 with the central channel 12.

To create a long-lasting compound concentration gradient in the device, all channels and reservoirs are filled with medium. A first step is to introduce equal amounts of a first fluid, in this case a cell culture medium having a first compound concentration into the first side channel 14 and a second fluid, in this case a cell culture medium having a second compound concentration into the second side channel 16. The second concentration of the second fluid is selected to be less than the first compound concentration, for example the second concentration may be zero and the first concentration may be non-zero.

In further detail, a volume of the first fluid equal to a first volume is introduced into the first reservoir 22 of the first side channel and a volume of the first fluid equal to the first volume is introduced into the second reservoir 24 of the first side channel. A volume of the second fluid equal to the first volume is introduced into the first reservoir 26 of the second side channel and a volume of the second fluid equal to the first volume is introduced into the second reservoir 28 of the second side channel. Fluid may be introduced by any suitable method, for example, by injection or pipetting.

A second step is to introduce a volume of the second fluid into the central channel, wherein the volume introduced is smaller than the volume introduced into the side channels. In further detail, a volume of the second fluid equal to a second volume is introduced into the first central reservoir 18 and a volume of the second fluid equal to a second volume is introduced into the second central reservoir 20. Since the second volume is less than the first volume and due to the dimensions of the reservoirs, the first volume of fluid fills the side reservoirs to a height that is greater than the height of the second volume of fluid in the central reservoirs.

The compound concentrations of the first and second fluids provide a measure of an amount of compound present in the fluid per unit volume of fluid.

While only two concentrations are described above, more than two different fluids, each having a different compound concentration may be used. For example, a first fluid having a first compound concentration may be introduced to the first reservoir, a second fluid having a second compound concentration may be introduced to the second reservoir, a third fluid having a third compound concentration may be introduced to the third reservoir and a fourth fluid having a fourth compound concentration may be introduced into the fourth reservoir.

In another example, the fluids may contain more than one different compound such that, for example, the first fluid has a first compound at a first concentration and a second compound at a second concentration.

The compound may be selected to have a positive effect or a negative effect on at least a portion of a cell sample. For example, the compound may be a drug for use in treatment, cure, prevention or diagnosis of disease or otherwise be a compound that has an enhancing effect on a cell sample. In this case the fluid comprising the drug is a drug solution with a drug concentration. Alternatively, the compound may be selected to provide a chemical stimulus to at least a portion of a cell sample. For example, the compound may be a chemical for providing a negative effect to a least a portion of the cell sample for studying the spread of said negative effect to the rest of the cell sample. In one example, the compound and corresponding compound gradient may be selected to cause damage to at least a portion of a cell sample allowing study of spread of damage and/or toxicity in the sample and cell network communications.

As illustrated in FIG. 4, following the introduction of first fluid and second fluid, there is provided a column of first fluid at a first height in each of the side reservoirs 22, 24, 26 and 28 and a column of second fluid at a second height in each of the central reservoirs 18 and 20. A column of fluid at the first height exerts a first hydrostatic pressure and a column of fluid at the second height exerts a second hydrostatic pressure. Fluid present in the first and second side channels 14, 16 is therefore under a first hydrostatic pressure and fluid present in the central channel 12 is under a second hydrostatic pressure.

The difference in fluid heights of the reservoirs is a result of the volume of fluid injected into the reservoirs and the dimensions of the reservoirs. Since the second height has a lower value than the first height, the first hydrostatic pressure has a greater value that the second hydrostatic pressure. Due to the height difference of the fluid in the first reservoir and the fluid in the second reservoir, labelled by $\Delta h$, a hydrostatic pressure gradient is therefore present between each of the side channels and the central channel. In other words, the pressure in the side channels is greater than the pressure in the central channel. The hydrostatic pressure difference between the first side channel 14 and the central channel 12 generates a first fluid flow in the direction from the first side channel 14 to the central channel 12. The hydrostatic pressure difference between the second side channel 16 and central channel 12 generates a second fluid flow in the direction from the second side channel 16 to the central channel 12. The generated flows, in combination with compound diffusion, create a microfluidic concentration gradient across the micro-well array provided in the central channel 16. The concentration gradient is provided perpendicular to the central channel 12. The concentration gradient can be established to be substantially continuous or substantially non-continuous as described, in further detail, with reference to FIG. 6.

The effect of the overflow opening and plug is now described. With the overflow plugs in place, the overflow openings are closed. As described above, hydrostatic gradients, cause the compound solution in the reservoirs of the first side channel 14 to flow to the central channel 12 via the first side channel 14 and micro-channels 36. Likewise, cell medium flows from the reservoirs of the second side channel 16 to the central channel 12 via the second side channel 16 and micro-channels 36. The compound solution and medium then flows through the central channel 12 to the reservoirs of the central channel. As result of this movement of fluid, the volume of fluid in the reservoirs of the side channels decreases and the volume of fluid in the reservoirs of the central channel increases. Because each of the reservoirs of the side channels are designed to be at least larger than the volume of the central channel reservoirs, for example at least 4 times the capacity size, and because the micro-channels offers a high hydraulic resistance to fluid flow, the fluid level of fluid in the reservoirs of the side channels decreases at a lower rate than the corresponding increase of fluid level in the reservoirs of the central channels. Therefore, the height difference between the fluid in the side channel reservoirs and the fluid in the central channel reservoirs tends to zero. The disappearance of height difference causes a cessation of fluid flow. This results in a loss of concentration gradient, because molecular diffusion dominates over convective flow. Therefore, the concentration gradient is short in duration with the overflow plugs present.

With the overflow plugs absent, the overflow openings are thus open. Hydrostatic gradients, created as described above, cause the compound solution in the reservoirs of the first side channel 14 to flow to the central channel 12 via the first side channel 14 and micro-channels 36. Likewise, cell medium flows from the reservoirs of the second side channel 16 to the central channel 12 via the second side channel 16 and micro-channels 36. The compound solution and medium then flows through the central channel 12 to the reservoirs of the central channel 12. The volume of fluid in the reservoirs of the side channels decreases and the volume of fluid in the reservoirs of the central channel increases. In contrast to the case without overflow openings, when the fluid contained in the reservoirs of the central channels 14, 16 reaches the height of the overflow opening, it is output to a waste channel. Therefore the maximum height of fluid stored in these reservoirs is limited to the height of the overflow opening. The hydrostatic pressure of the central channel is also limited. Once the maximum height, the height of the overflow opening, is reached, the hydrostatic pressure of the central channel remains constant as excess fluid exits the device 10 through the overflow opening. By limiting the height, the height difference decreases at a substantially slower rate than in the case without overflow openings. Therefore, the pressure difference between the side channels and the pressure channels decreases very slowly relative to the case without overflow openings. The pressure in the central channel and/or the central reservoirs is substantially maintained and/or for example, may change at a rate below a predetermined threshold rate. A concentration gradient is formed that is substantially maintained over a longer period of time than the concentration gradient formed without the overflow openings. A change to the geometry of the micro-channel and central channel may also change the duration of the concentration gradient.

Following completion of drug delivery assay, the reservoirs containing compound are then emptied to avoid cross contamination in the central channel. Only cell culture medium is refreshed. The overflow plugs may be replaced to continue cell culturing.

The shape and dimensions of the network of micro-channels is important for the creation of a specific shape of compound concentration gradient across the micro-well array. The network of micro-channels may have at least one common dimension as the micro-well array. For example, the width of each micro-channel may be the same as the width of a micro-well array column or row, such that, each micro-channel is positioned to be directly coupled to a corresponding micro-well column or row.

As a non-limiting example, the first volume of first fluid is 200 micro-litres of a drug solution that is pipetted into the first reservoir 22 of the first side channel 14 and the second reservoir 24 of the first side channel 14. The same volume of cell culture medium without drugs is pipetted into the first reservoir 26 of the second side channel 16 and the second reservoir 28 of the second side channel 16. A smaller volume of cell culture medium without drug of 25 micro-litres is pipetted into the first central reservoir 18 and second central reservoir 20. This protocol results in a greater fluid height in side reservoirs 22, 24, 26 and 28 than in central reservoirs 18, 20 which correlates with a differential hydrostatic pressure between side channels and the central channel. In this example device, a concentration gradient is formed and substantially maintained. In this example, the concentration gradient is maintained for at least 16 hours, changing less than 10% from its initial steady state value (~2 hours after injection).

Figure 5:
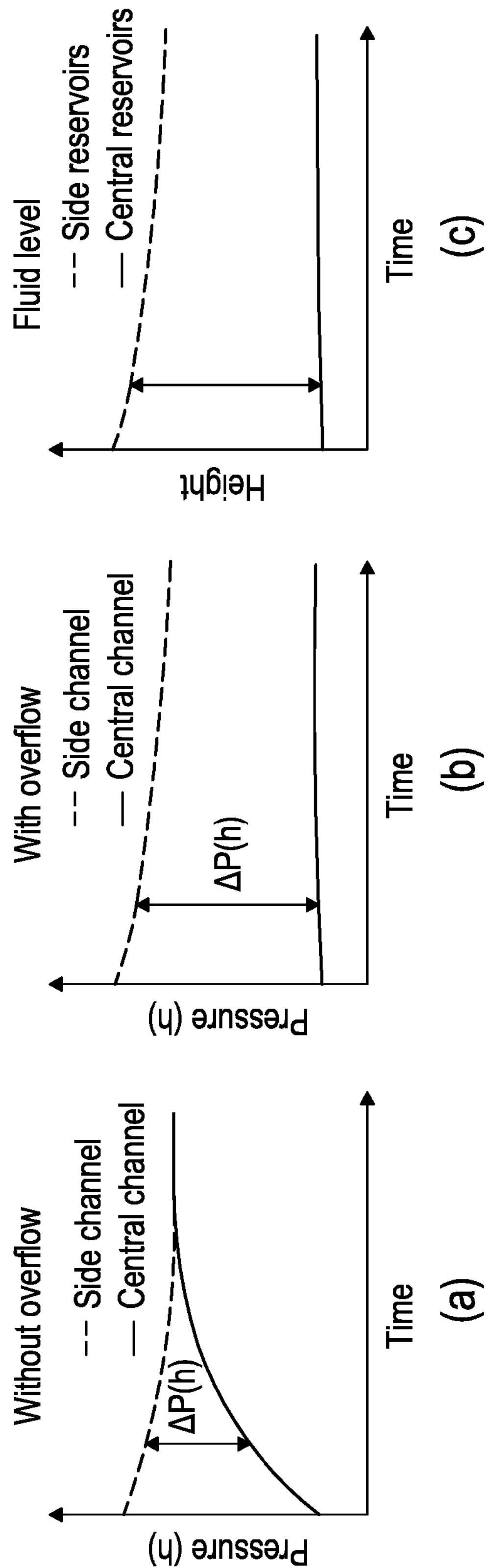
FIG. 5 shows a series of plots illustrating change in pressure and change in fluid level with time.

FIG. 5 shows a series of plots illustrating behaviour of the device over time. FIGS. 5(*a*) and 5(*b*) show plots of the change of hydrostatic pressure in one of the side channels and the central channel over time when the overflow plugs 34 are present (FIG. 5(*a*)) and when the overflow plugs 34 are absent thus exposing the overflow openings 30, 32 (FIG. 5(*b*)). The upper curve of both plots illustrates the change in hydrostatic pressure with time in the side channel and the lower curve of both plots illustrates the change in hydrostatic pressure with time in the central channel.

FIG. 5(*a*) shows that when the overflow plug is present, the pressure difference between the side and central channels tends to zero as the pressure in the central channel rises quickly to equilibrate to the pressure in the side channels. This is undesirable, as a compound gradient is only produced for a short duration of time and is not substantially maintained. FIG. 5(*b*) shows that if the overflow plug is absent and thus the overflow opening is exposed, the pressure in the central channel is maintained at an approximately constant value. The pressure difference between wells decreases at a much lower rate of change relative to the case with no overflow opening over an extended period of time and can therefore be considered to be substantially maintained. Therefore, the pressure difference between the side channel and central channel is maintained at a substantially constant value for a period of time. This allows for a stable compound concentration gradient to be established for an extended period of time.

FIG. 5(*c*) shows the fluid level in the side reservoirs and the central reservoir and how these levels change in time, with the overflow openings open. The upper curve shows the change over time of the fluid level in the side reservoir and the lower curve shows the change over time of the fluid level in the central reservoir.

Use of the device can be controlled to establish different shapes of concentration gradient across the micro-well for different purposes. Generally, a concentration gradient that is substantially non-continuous across the micro-well array or substantially continuous across the micro-well array can be established. By virtue of the compound concentration gradient, cells within the micro-wells are exposed to different chemical concentrations across the width of the central channel. The shape of the gradient is dependent on the amplitude of the pressure difference between the side channel and the central channel, ΔPh. Therefore the shape of the gradient is controlled by the respective volumes to be introduced in the wells. Different shapes of concentration gradients can be used for different shapes and arrangements of the array of micro-wells, for example those shown in FIG. 3 and thus for different experimental purposes.

Values can be obtained by using larger volumes in the well by making the well taller (greater than 1 mL) but also by making the cross section of each of the micro-channels in the array larger. This creates a faster flow in the central channel and progressively sharper concentration gradient shapes. Alternatively, and only for the sharp gradient formation, syringe pumps can be connected to the inlet of the two side channel and applying volumetric flow rates in the range of 0.1 to 2 micro litre per minute.

Figure 6:
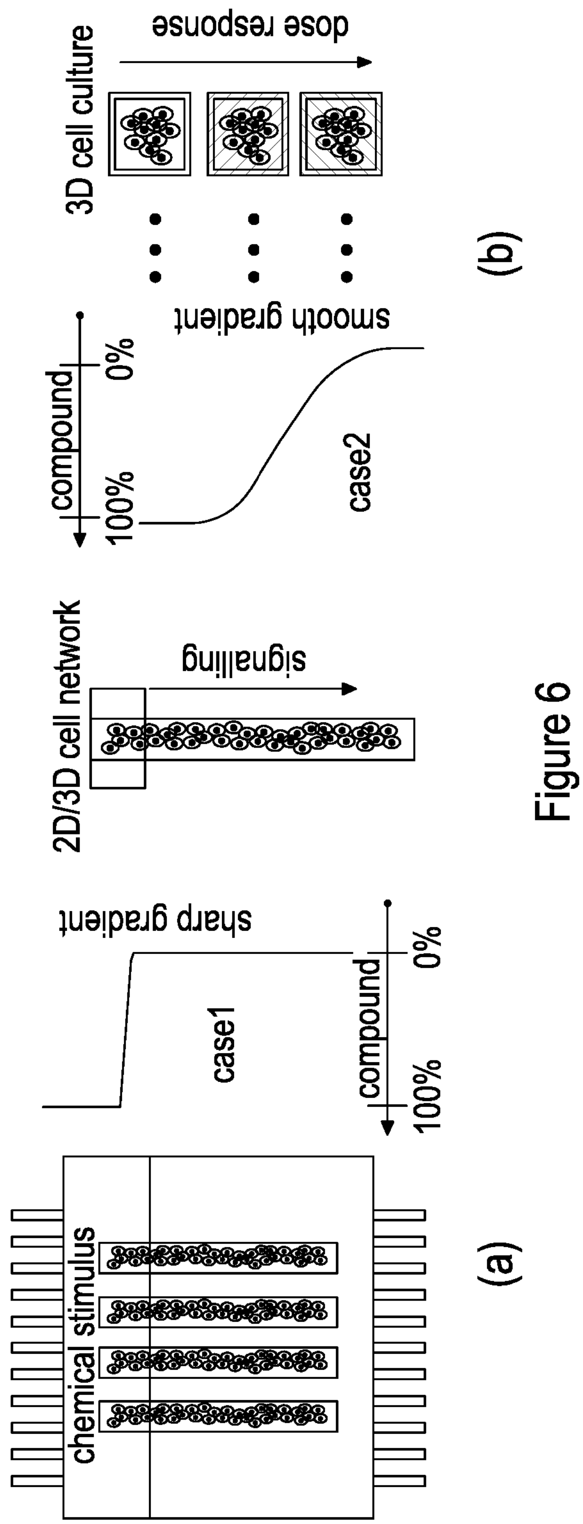
FIG. 6 shows two examples of a compound concentration gradient, in particular a sharp gradient and a linear gradient, generated in the microfluidic device.

FIG. 6(*a*) shows a first example where a sharp compound concentration gradient is generated for rectangular micro-wells, for example those shown in FIG. 3(*a*). The compound concentration gradient shown in FIG. 6(*a*) is an example of a substantially non-continuous compound concentration gradient. In this example, only a small number of cells within the rectangular wells are exposed to a chemical stimulus, at a first end, which generates an effect that can be used to study spread of toxicity to the unexposed cells. Using this gradient, damage can be applied only to a portion of the cell network and this approach allows new assays to be performed on either 2D cell networks or 3D oblong multicellular structures to study in a completely unprecedented way spreading toxicity and cell network communications in 3D.

A second example is shown in FIG. 6(*b*) where a linear gradient is generated using a rectangular array of square micro-wells, for example those shown in FIG. 3(*b*). The compound concentration gradient shown in FIG. 6(*a*) is an example of a substantially continuous compound concentration gradient. The micro-well array may also be a rectangular array of circular micro-wells. A linear gradient enables concentration response curves to be produced by averaging the response of each spheroid in the same row, over multiple columns, whilst assessing the responses for different concentration in each row. This allows new assays to be performed for personalised medicine therapeutics, maximising the use of single tumour biopsies using 3D micro-tumours.

Figure 7:
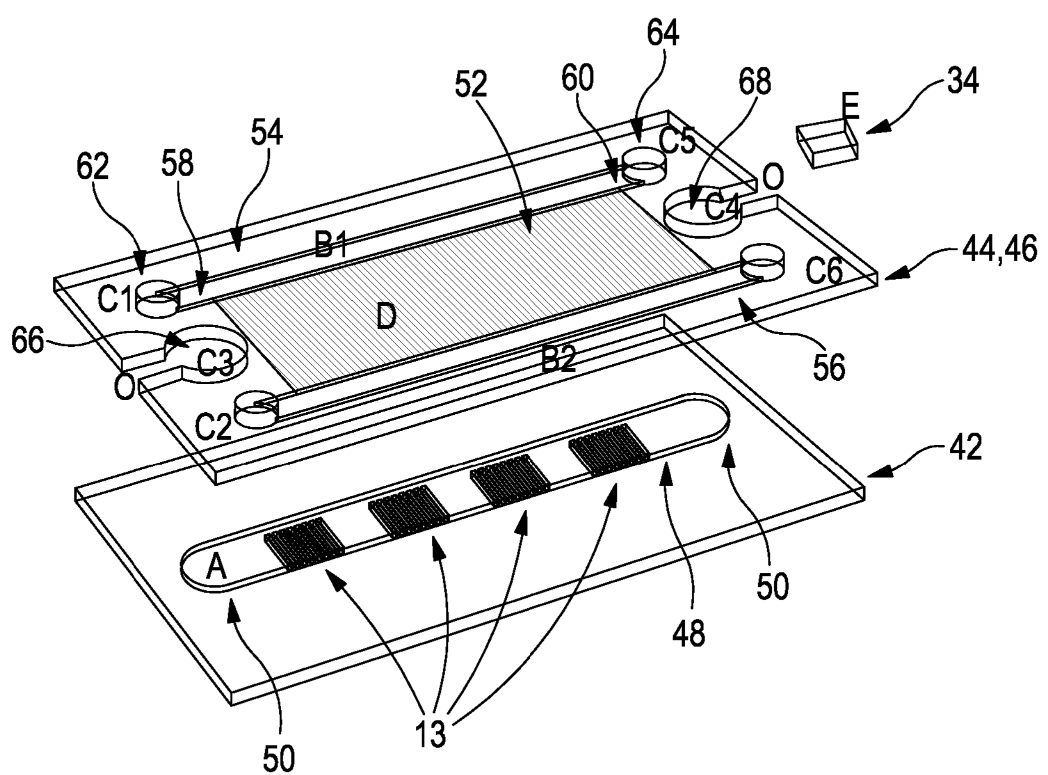
FIG. 7 is an exploded perspective view of the microfluidic device in a disassembled configuration.

FIG. 7 shows an exploded view of the device 10 in a disassembled configuration. The device 10 has three layers: a base layer 42, a middle layer 44 and an upper layer 46. The base layer 42, middle layer 44 and upper layer 46 are sized and configured to fit together to form the device 10. This connection may be provided by a plurality of connectors provided on the different layers.

FIG. 7 shows the middle layer 44 and upper layer 46 fitted together. In the assembled configuration, the middle layer 44 is placed on the lower layer 42 and the upper layer 46 is placed on the middle layer 44.

The base layer 42, consider alone, is formed from a flat cartridge. A trench 48 extends along the base layer 42. The trench 48 is straight and has a trench bed at a uniform trench depth along its length. The trench 48 is a groove cut out of the base layer 42 to the trench depth. The groove has a trench wall surrounding its perimeter. The trench 48 has two end regions 50 provided at its first and second ends, respectively. For ease of manufacture, the end regions 50 have a depth equal to the trench depth and therefore part of the trench wall surrounds part of the end regions 50. As the end regions 50 are circular in shape, each end region 50 has a semi-circular trench wall. The two semi-circular trench walls oppose each other. The trench 48 and its end regions provide an open channel in the base layer 42. When assembled, the trench and its end regions comprise part of the central channel 12 and associated reservoirs 18, 20, as described with reference to FIG. 1.

FIG. 7 shows the four arrays of micro-wells 13 suitable, for example, for the culture of 3D multicellular spheroids, formed in the bed of the trench 48. Each array of micro-wells 13 is formed such that the micro-wells are underneath the bed level but open to the trench 48.

The middle layer 44 has an array of dividing walls 52 that act as side-walls for an array of open passages that are open at the top and bottom. The dividing walls are parallel and run across the middle layer 44. Relative to the base layer 42, the array of side-walls are provided in a perpendicular direction to the length of the trench 48 of the base layer 42. When the middle layer 44 is fitted to the base layer 42, the side-walls 52 overlay the trench 48.

In the assembled configuration, the open passages act as part of the network of micro-channels 36, as described with reference to FIG. 1. The array of micro-channels is formed by the lower surface of the upper layer 46, the upper surface of the lower layer 42 and the dividing walls 52. In particular, the lower surface of the upper layer 46 provides a ceiling for the micro-channels 36 and the upper surface of the lower layer 42 provides a floor for the micro-channels 36.

Each open passage is open at the top and bottom and at both its ends. In the assembled configuration, the passages form the micro-channels that overlay the trench 48 which is provided in lower layer 42 and each micro-channel is open to the trench 48 in a middle section. This opening allows fluid communication between the micro-channels and the trench 48.

The trench 48 of the lower layer 42 has a floor and two parallel side walls. In the assembled configuration, the dividing walls 52 provided in the middle layer 44 provide a partially enclosed roof to the trench thereby forming the central channel 12.

The upper layer 46 or top layer creates a structure of channels and open wells used for cell seeding and drug injection. The open wells create fluid reservoirs connected to the channels with their diameter and height varying according to the shape of the concentration gradient to be created. The upper layer 46 is a flat cartridge of same width and length as the base layer 42. The upper layer 46 has a first partially enclosed side passage 54 and a second partially enclose side passage 56 extending parallel to each other along the length of the upper layer 46. In the assembled configuration, the partially enclosed side passages 54 and 56, together with the base layer 42 form the side channels 14 and 16, as described with reference to FIG. 1.

The two partially enclosed side passages are provided at a separation distance equal to the length of the dividing walls 52 of the middle layer 44, such that, in the assembled configuration, the micro-channels 36 are in fluid communication with the side channels.

The first side passage 54 is enclosed by a first side wall along its length. The side wall has a height that defines a depth of the side channel. A ceiling is also provided along the length of the side channel. The first side passage is therefore open along its floor and, and at least in part, along its second side. In the assembled configuration, a floor is provided by the upper surface of the lower layer 42. Alternatively, the side channel may be closed along its base by a floor provided in the upper layer 46.

At both ends of the first side passage 54 there is provided first and second peripheral walls 58, 60. The peripheral walls extend collinear to each other and both are parallel to the first side wall. An imaginary line can therefore be drawn collinear to the lengths of the peripheral walls which is parallel to the first side wall. Along this imaginary line and located between the two peripheral walls the side passage 54 has an open region.

In the assembled configuration, the open region of the side passage 54 couples to the array of dividing walls 52 of the middle layer 44 such that the dividing walls extend perpendicular to the side passage 54. The end points of the dividing walls 52 thus form a discontinuous side wall opposing the first side wall of the side passage 54. The side passage 54 is therefore partially enclosed by the discontinuous side wall and the upper surface of the lower layer 42 to provide the first side channel 14, as described with reference to FIG. 1. In summary, in the assembled configuration, the first side channel 14 is partially contained by its floor, which is provided by the upper surface of the base layer 42, by its ceiling, which is provided in the upper layer 46, along its first side by a first side wall and along its second side by the discontinuous side wall provided by the middle layer 44.

Returning to the disassembled configuration, at a first end of the side passage 54, adjacent to the first peripheral wall 58, there is provided a first cylindrical hole 62 and at a second end of the side passage 54, adjacent to the second peripheral wall 60, there is provided a second cylindrical hole 64. The first and second cylindrical holes are formed through the depth of the upper layer 46. Each cylindrical hole is open to the side passage via a side passage opening that has an equal depth to the depth of the side passage. In the assembled configuration, the first cylindrical hole 62 and base layer 42 form the first side reservoir 22. The upper surface of the base layer 42 provides a floor for the first side reservoir 22.

The second side passage 56 is provided as described with reference to the first side passage 54, but opposing the first side passage 54 such that there is a central region between the side passages.

The upper layer 46 has two further cylindrical holes. A first central cylindrical hole 66 and a second central cylindrical hole 68 are formed through the depth of the upper layer 46. The central holes are therefore open at their top and bottom. The central holes are provided in the central region between the side passages. In particular, the central holes are located on the upper layer 46 at the same location that the circular end regions 50 are provided on the base layer 42. In the assembled configuration the cylindrical holes 66, 68 coincide with the circular end regions 50 to form the two central reservoirs 18 and 20 associated with the central channel 12. In further detail, the circular end regions 50 of the lower layer 42 provide a base for the central reservoirs. The inner surface of the cylindrical holes and the semi-circular trench wall on the base layer 42 provide the inner walls of the reservoirs. A void that has the same depth as the trench wall is provided opposite the semi-circular trench wall. The void of the first cylindrical hole 66 and the corresponding void of the second cylindrical hole 68 provide the openings between the central channel 12 and its associated central reservoirs 18, 20.

Overflow slots are provided on both ends of the upper layer 46 that extend into the central holes 66, 68. The central hole and slot together provide a key-hole shaped opening. The slots are formed by cutting out rectangular overflow plugs from the upper layer. The overflow plugs are retained. The overflow plugs are insertable and removable from the overflow slots. In the assembled configuration, the overflow slots of the upper layer have a base provided by the upper surface of the lower layer 42 to form the overflow openings 30 and 32 of the central reservoirs 18 and 20. The overflow openings have the depth of the upper layer 46. In the assembled configuration, the overflow plugs can be inserted into the overflow openings and sit on the base provided by the upper surface of the lower layer 42. Alternatively, the plugs may have a depth less than the depth of the upper layer.

While FIG. 7 shows the device 10 as having three layers, alternatively, the device 10 may have two parts. For example, the device may have a top layer which corresponds to the upper layer 46 and middle layer 44 and a bottom layer corresponding to the lower layer 42. In this example, the top layer has micro-channels and inlets that enable cell seeding, medium exchange and drug application and the bottom layer has micro-wells for spheroid generation and culture. As a further example, the device may have a top layer which corresponds to the upper layer 46 and a bottom layer that corresponds to the middle layer 44 and a lower layer 42.

Figure 8:
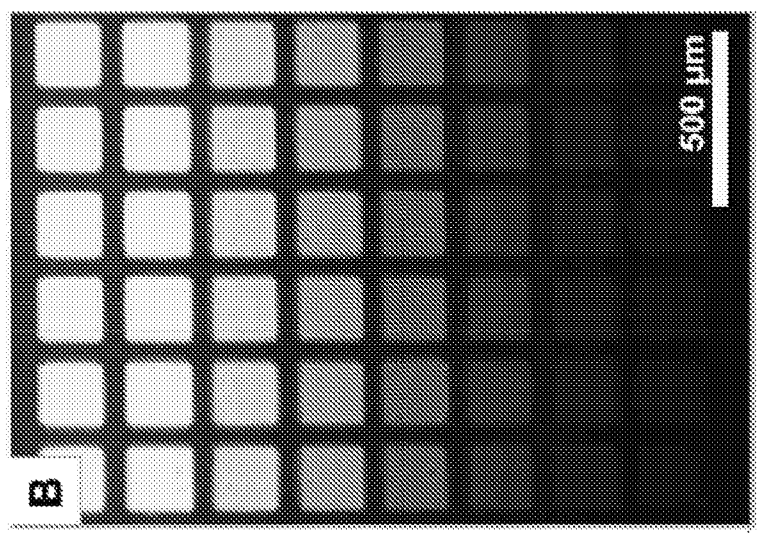
FIG. 8 illustrates formation and duration of a dye concentration gradient in the microfluidic device.
Figure 8:
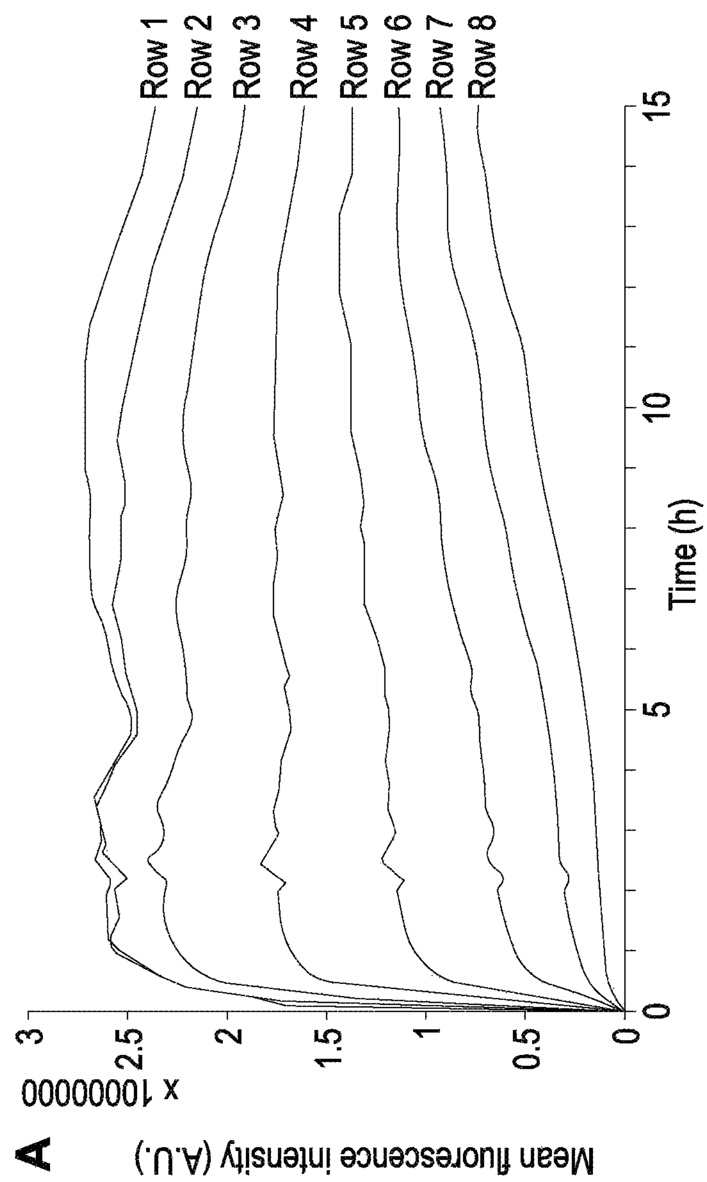

To demonstrate the robustness of the device operation, a fluorescent dye was used to visualise the formation and duration of a dye concentration gradient in the device monitored using fluorescence microscopy and time-lapse imaging. The results are shown in FIG. 8. The micro-well array was imaged every 3 minutes over the course of 15 hours, as shown in FIG. 8(*a*) which showed that a concentration gradient can be achieved within 2 hours and maintained for more than 12 hours with the current device geometry. In further detail, FIG. 8(*a*) shows average fluorescence intensity recorded in each row of micro-wells after application of a concentration gradient of calcein, over the course of 15 hours.

Numerical simulations confirm this experimental data and can be used to change the device geometry to estimate the gradient shape and duration. Considering the chemical's molecular weight, charts can be created for each drug tested. An example is shown in FIG. 8(*b*) which shows a calcein gradient in the device after 10 hours. The results demonstrate the administration of different concentrations of a chemical reagent to each row of the micro-wells, whilst all the micro-wells within the same row receive the same concentration. When applied to cancer spheroids and a cancer therapy drug, each of the eight rows of spheroids receives a different drug concentration. All the responses from spheroids in the same row can be used as replicates for the same drug concentration. For example, if the device has 8 row and 30 columns, this combination can be used for the generation of concentration response curves for drug efficacy testing small cell samples, such as patient biopsy tissue. This approach is efficient and the acquisition of a concentration response curve from the microfluidic device using spheroids is unique.

Figure 9:
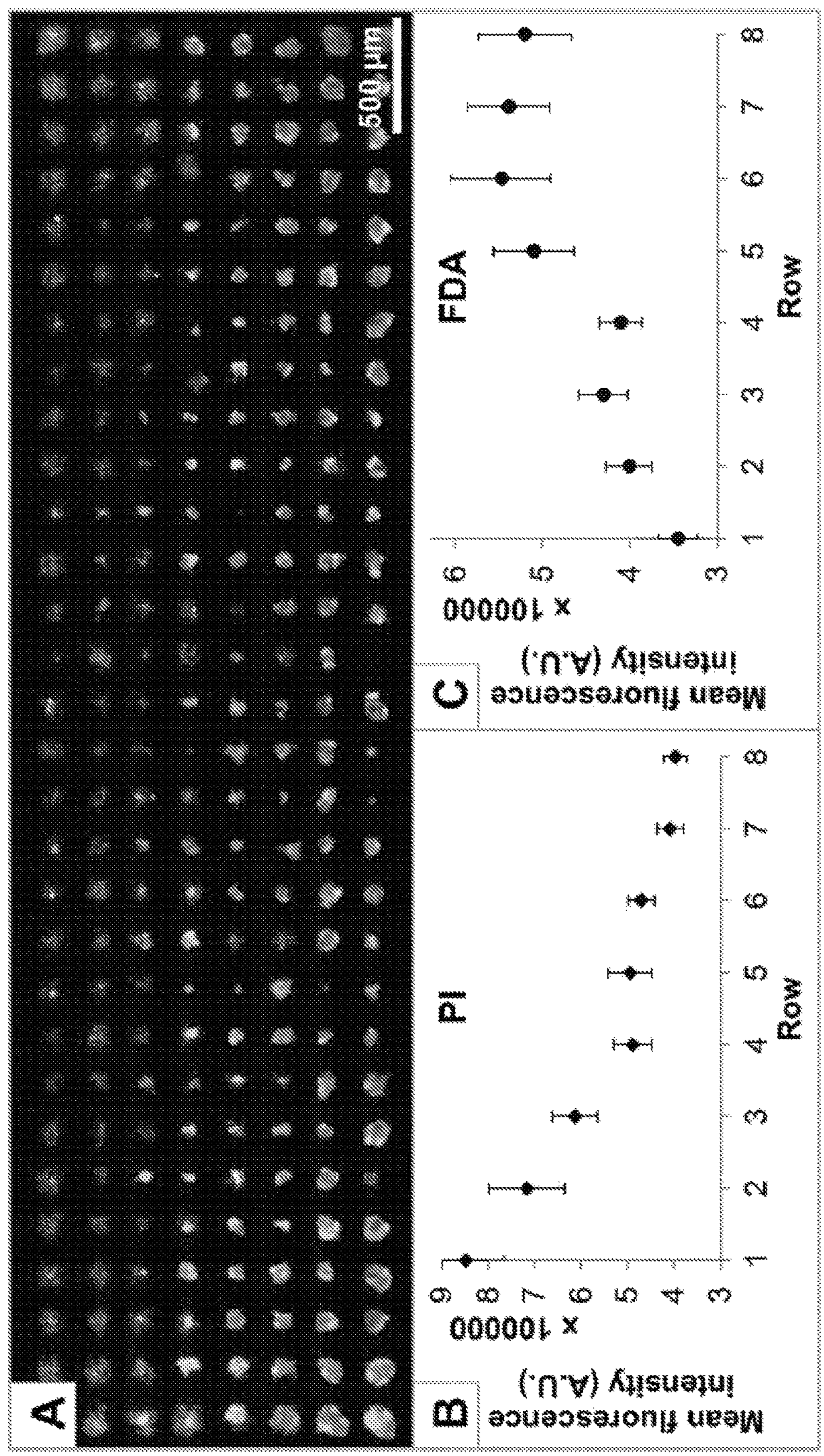
FIG. 9 illustrates fluorescence intensities measured in the micro-well array, and FIG. 10(*a*) shows a 2D cell network formed in an array of micro-wells of the device and FIG. 10(*b*) shows a 3D cell network formed in an array of micro-wells of the device.

FIG. 9 shows application of cisplatin gradient to an array of UVW glioma spheroid. To confirm that a drug concentration gradient can be applied to 3D tumour spheroids in the device, cisplatin, a chemotherapy drug, was used. Suitable volumes for the use of cisplatin were determined using simulations. Cisplatin's molecular weight=300 Da, which is less than half the molecular weight of calcein (623 Da). As the weight is less, cisplatin diffuses much quicker than calcein, and the volumes to be injected into all reservoirs need to be adjusted accordingly.

3D spheroids were generated from UVW cells and cultured for 5 days, after which a 175 μM cisplatin solution was pipetted into the side reservoirs 22, 24 of the first side channel 14. Medium was pipetted into central reservoirs 18, 20 of the central channel 12. The device 10 was then incubated for 15 hours without being monitored. Subsequently, the cisplatin was washed out and replaced with cell medium. After a further 2 days, the viability of the UVW spheroids was assessed. The results are shown in FIG. 9(*a*). Fluorescent viability dye, fluorescein diacetate (FDA) was used for live cells (green) and propidium iodide (PI) was used for dead cells (red). The fluorescence intensity of PI and FDA was determined in each micro-well using image analysis.

FIG. 9(*b*) shows average fluorescence intensity of PI for each row of micro-wells. FIG. 9(*c*) shows average fluorescence intensity of FDA in each row of micro-wells. Average fluorescence intensity of PI and FDA in each row was obtained by quantifying fluorescence intensity in each micro-well. The results show that increasing cisplatin concentrations correlate well with an increase in dead cells (PI) and a decrease in live cells (FDA). It can be concluded that a concentration-response curve for a drug can be obtained from the microfluidic device described here using less than 50,000 cells per device.

Figure 10:
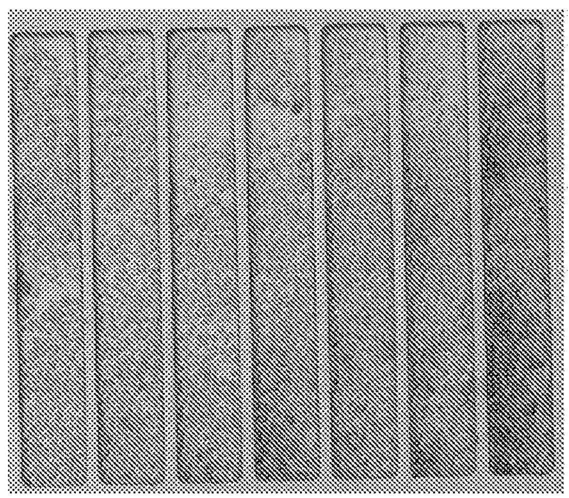
Figure 10:
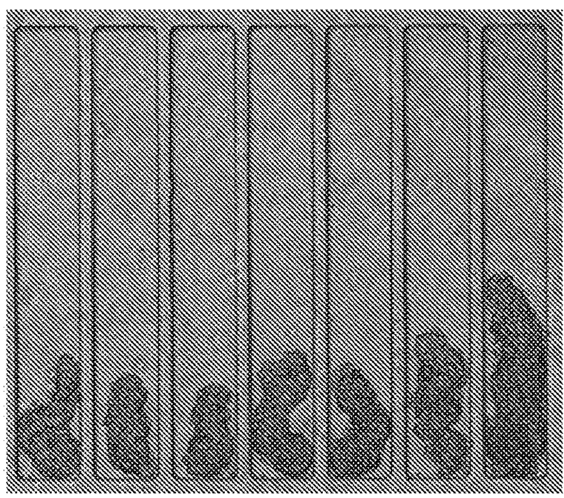

FIG. 10(*a*) shows a 2D cell networks formed in each micro-well of the array of micro-wells the device. FIG. 10(*b*) shows 3D cell networks formed in each micro-well of the array of micro-wells of the device.

The proposed device advantageously enables the generation and culture of thousands of 3D spheroids, for example, micro-tumours, derived from patient biopsies, thus allowing drug screening to be performed on physiologically relevant tumour models and maximising the number and quality of information that can be extracted from tumour tissues (since biopsies often only provide a limited number of cells). The proposed microfluidic device with overflow opening enables the formation of long-lasting, compound concentration gradients (12-24 hours) to be applied on an array of spheroids without the need of connected external instrumentation. The device can also be designed to comply with well plate formats (i.e. 96 or 384 well plate dimensions and well pitch for interfacing with plate readers) and can be directly interfaced with robotic dispensers used in industry. Plates can be used with high-throughput instrumentation.

By creating differences in fluid heights across the open reservoirs of the device, and consequently creating differences in hydrostatic pressure, cells and/or compound transport is obtained in a completely predictable manner across the channel network. In addition, the device allows a substantially constant and stable pressure gradient to be maintained without using controlled syringe pumps which increases the complexity and costs of the setup for multiple devices. Operation of the present device relies only on the geometry of the device.

The device allows screening of patient-derived 3D spheroids in a high-throughput manner. The device has applications in personalised medicine, drug and combination chemo- and radio-therapy screening and functional assays.

The device may be fabricated using at least one of polydimethylsiloxane (PDMS), polystyrene or polycarbonate material.

A skilled person will appreciate that variations of the enclosed arrangement are possible without departing from the invention. Accordingly, the above description of the specific embodiment is made by way of example only and not for the purposes of limitations. It will be clear to the skilled person that minor modifications may be made without significant changes to the operation described.

The invention claimed is:

1. A microfluidic device comprising:

a main body;

at least one source reservoir and at least one collection reservoir, wherein the at least one collection reservoir comprises an inlet at an upper surface of the main body for introducing fluid to said reservoir;

at least one fluid channel for channelling a fluid comprising a compound from the at least one source reservoir to the at least one collection reservoir;

a plurality of chambers for holding cells, wherein the plurality of chambers are formed underneath and open to the fluid channel, wherein a fluid flow is generated through the at least one fluid channel by a difference in hydrostatic pressure between fluid in the at least one source reservoir and fluid the at least one collection reservoir such that the fluid flow provides a compound concentration gradient across the plurality of chambers and wherein the at least one collection reservoir has an overflow opening coupled to the collection reservoir, wherein the overflow opening comprises a slot having a depth, said slot extending into the inlet of the at least one collection reservoir such that fluid collected in the collection reservoir is configured to reach the height of the overflow opening the fluid is output via the overflow opening thereby to maintain a level of hydrostatic pressure in the at least one collection reservoir.

2. A microfluidic device as claimed in claim 1 further comprising:

a removable overflow plug sized to close the overflow opening when inserted into the overflow opening.

3. A microfluidic device as claimed in claim 1, wherein at least one reservoir of the at least one source reservoir and the at least one collection reservoir comprises an inlet for introducing fluid to said reservoir.

4. A microfluidic device as claimed in claim 1, wherein the at least one fluid channel further comprises:

a collection channel coupled to the at least one collection reservoir wherein the plurality of chambers are provided in the collection channel, and a plurality of further channels in fluid communication with the at least one source reservoir and coupled to the collection channel for channelling fluid from the at least one source reservoir to the collection channel.

5. A microfluidic device as claimed in claim 4 wherein the plurality of further channels comprises at least one microchannel.

6. A microfluidic device as claimed in claim 4 wherein the at least one fluid channel comprises at least one secondary channel coupled to the at least one source reservoir and arranged to be substantially parallel to the collection channel, and wherein the plurality of further channels couple the at least one secondary channel to the collection channel.

7. A microfluidic device as claimed in claim 6, wherein the at least one secondary channel comprises two secondary channels positioned on either side of the collection reservoir.

8. A microfluidic device as claimed in claim 4, wherein the collection channel is coupled to two collection reservoirs.

9. A microfluidic device as claimed in claim 1, wherein the at least one source reservoir is sized to have a greater fluid capacity than the at least one collection reservoir.

10. A microfluidic device as claimed in claim 9, wherein the at least one source reservoir is sized to have an at least four times greater fluid capacity than the at least one collection reservoir.

11. A microfluidic device as claimed in claim 1, wherein the chambers of the plurality of chambers are square, round, rectangular and/or oblong in shape.

12. A microfluidic device as claimed in claim 1, wherein the plurality of chambers are arranged in an array having one or more columns and one or more rows.

13. A microfluidic device as claimed in claim 1, wherein each chamber of the plurality of chambers has a volume in the range of 100 to 400 micrometres cubed.

14. A microfluidic device as claimed in claim 1, wherein the device comprises at least one of polydimethylsiloxane (PDMS), polystyrene or polycarbonate.

15. A microfluidic device as claimed in claim 1, wherein interior surfaces of the device are non-adherent.

16. A microfluidic device as claimed in claim 1, wherein the compound concentration gradient across the plurality of chambers is substantially continuous or substantially non-continuous.

17. A kit of parts to be assembled to form the microfluidic device of claim 1, said kit of parts comprising:

a lower layer and an upper layer sized to permit connection.

18. A kit of parts as claimed in claim 17, further comprising:

a middle layer sized to permit connection to the upper layer and to the lower layer.

19. An assay system comprising:

at least one first microfluidic device of claim 1;

imaging means for imaging seeded cells in the at least one microfluidic device; and a well plate.

20. A method comprising:

seeding cells in a plurality of chambers formed underneath and open to a fluid channel, wherein the fluid channel is configured to channel fluid from at least one collection reservoir to at least one source reservoir, wherein the at least one collection reservoir comprises an inlet;

providing an overflow opening in the at least one collection reservoir wherein the overflow opening is coupled to the at least one collection reservoir and comprises a slot having a depth, said slot extending into the inlet of the at least one collection reservoir;

providing the at least one collection reservoir with a first volume of a first fluid via the inlet and providing the at least one source reservoir with a second volume of a second fluid, wherein the second fluid comprises a compound, such that a fluid flow is generated by a difference in hydrostatic pressure between the first volume of first fluid in the at least one collection reservoir and the second volume of second fluid in the at least one source reservoir thereby providing a compound concentration across the plurality of chambers, wherein fluid exits through the overflow opening in the at least one collection reservoir when the fluid in the at least one collection reservoir reaches the height of the overflow opening thereby to maintain a level of hydrostatic pressure in the at least one collection reservoir.

21. A method as claimed in any of claim 20, wherein the measurement of a response is performed after a first period of time.

22. A microfluidic device as claimed in claim 7, wherein each of the at least one secondary channels is coupled to two source reservoirs.

23. A microfluidic device as claimed in claim 7 wherein the collection channel is coupled to two collection reservoirs and each of the at least one secondary channels is coupled to two source reservoirs.

* * * * *